US010435443B2

(12) United States Patent
Choi et al.

(10) Patent No.: US 10,435,443 B2
(45) Date of Patent: Oct. 8, 2019

(54) TOLL-LIKE RECEPTOR 4 (TLR4) ANTAGONIST

(71) Applicant: GENESEN CO., LTD., Seoul (KR)

(72) Inventors: Sangdun Choi, Suwon-si (KR); Tae Hyeon Yoo, Yongin-si (KR); Seol Hee Park, Uiwang-si (KR)

(73) Assignee: Genesen Co., Ltd., Seoul (KR)

(*) Notice: Subject to any disclaimer, the term of this patent is extended or adjusted under 35 U.S.C. 154(b) by 0 days.

(21) Appl. No.: 15/578,094

(22) PCT Filed: Jul. 31, 2015

(86) PCT No.: PCT/KR2015/008055
§ 371 (c)(1),
(2) Date: Nov. 29, 2017

(87) PCT Pub. No.: WO2016/195159
PCT Pub. Date: Dec. 8, 2016

(65) Prior Publication Data
US 2018/0148487 A1  May 31, 2018

(30) Foreign Application Priority Data
May 29, 2015 (KR) .................. 10-2015-0076101

(51) Int. Cl.
| | | |
|---|---|---|
| C07K 7/00 | (2006.01) |
| C07K 7/08 | (2006.01) |
| C07K 14/47 | (2006.01) |
| C07K 16/28 | (2006.01) |
| A61K 38/04 | (2006.01) |
| A61K 38/10 | (2006.01) |
| A61P 29/00 | (2006.01) |
| A61P 37/00 | (2006.01) |
| A61K 38/00 | (2006.01) |

(52) U.S. Cl.
CPC .......... C07K 14/4703 (2013.01); A61P 29/00 (2018.01); A61P 37/00 (2018.01); C07K 7/08 (2013.01); C07K 14/47 (2013.01); A61K 38/00 (2013.01); C07K 16/2896 (2013.01)

(58) Field of Classification Search
CPC . C07K 7/00; C07K 7/08; C07K 14/47; C07K 14/4703; C07K 16/2896; C07K 16/28; A61P 29/00; A61K 38/04; A61K 38/10
USPC ........ 530/300, 326; 514/1.1, 6.9, 17.8, 12.2, 514/17.9, 18.6, 18.7, 19.2, 19.3, 21.4
See application file for complete search history.

(56) References Cited

U.S. PATENT DOCUMENTS

| | | | | |
|---|---|---|---|---|
| 7,351,881 B2 * | 4/2008 | Carozzi | ................ | C07K 14/325 800/302 |
| 7,745,391 B2 * | 6/2010 | Mintz | ..................... | G06F 19/24 514/19.3 |
| 2010/0069297 A1 | 3/2010 | Fenton et al. | | |

FOREIGN PATENT DOCUMENTS

| | | |
|---|---|---|
| KR | 10-2008-0065653 A | 7/2008 |
| KR | 10-2011-0119279 A | 11/2011 |
| WO | 2005/065015 A2 | 7/2005 |
| WO | 2009/059143 A2 | 5/2009 |
| WO | 2015/048083 A1 | 2/2015 |

OTHER PUBLICATIONS

Alzheimer Disease from Merck Manual, pp. 1-10. Accessed Nov. 27, 2018.*
Dementia from Merck Manual, pp. 1-13. Accesssed Jul. 29, 2009.*
Mattson MP, "Pathways towards and away from Alzheimer's disease," Nature, Aug. 2004, 430: 631-639.*
Introduction to Cancer from Merck Manual, p. 1. Accessed Mar. 5, 2008.*
Clinical Aspects of Cancer from Merck Manual, pp. 1-4. Accessed Mar. 5, 2008.*
Sporn et al, "Chemoprevention of cancer," Carcinogenesis, 2000, 21(3): 525-530.*
Auerbach et al, "Angiogenesis assays: Problems and pitfalls," Cancer and Metastasis Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, Jul. 1994, 58-65.*
Multiple Sclerosis from Merck Manual, pp. 1-11. Accessed Nov. 14, 2018.*
Rheumatoid Arthritis from Merck Manual, pp. 1-18. Accessed Apr. 21, 2016.*
Solid Cancer from Merck Manual, pp. 1-4. Accessed Nov. 27, 2018.*
Park et al, "TLR4/MD2 specific peptides stalled in vivo LPS-induced immune exacerbation," Biomaterials, (2017), 126, pp. 49-60.*
Svajger et al., "Novel Toll-Like Receptor 4(TLR4) Antagonists Identified by Structure- and Ligand-based Virtual Screening", European Journal of Medicinal Chemistry, vol. 70, pp. 393-399 (2013).
International Search Report of International Application No. PCT/KR2015/008055, "Novel TLR4 Antagonist", 3 pgs., dated Oct. 19, 2015.

(Continued)

*Primary Examiner* — Julia Ha
(74) *Attorney, Agent, or Firm* — Vorys, Sater, Seymour and Pease LLP; Mih Suhn Koh

(57) ABSTRACT

Provided is a peptide that binds to a toll-like receptor 4 (TLR4)/myeloid differentiation factor 2 (MD2) composite and inhibit secretion of interleukin-6 (IL-6), nitrogen monoxide (NO) and reactive oxygen species (ROS), and activation of nuclear factor kappa-light-chain-enhancer of activated B cells (NFκB) and mitogen-activated protein kinases (MAPKs) via inhibiting a TLR4 signaling pathway induced by a liphopolysaccharide (LPS); a TLR4 antagonist including the peptide; and a composition thereof for preventing or treating autoimmune diseases and inflammatory diseases.

12 Claims, 11 Drawing Sheets

Specification includes a Sequence Listing.

(56) References Cited

OTHER PUBLICATIONS

Written Opinion of International Application No. PCT/KR2015/008055, "Novel TLR4 Antagonist", 4 pgs., dated Oct. 19, 2015.
Choi "Study of innate immune system and development of new medicine by using Toll-like receptor agonists", Ministry of Education, Science and Technology (Jun. 2012).
Park "High Throughput Screening of Novel TLR4/MD2 Modulating Peptides through Phage Display System", Master's Thesis, Ajou University, 36 pages (2015).
Extended European Search Report for corresponding EP Application No. 15894332.4, dated Dec. 7, 2018, five pages.
Park et al., "TLR4/MD2 specific peptides stalled in vivo LPS-induced immune exacerbation", Biomaterials, 2017, vol. 126, pp. 49-60.

* cited by examiner

TOLL-LIKE RECEPTOR 4 (TLR4) ANTAGONIST

SEQUENCE LISTING

The Sequence Listing submitted in text format (.txt) filed on Jun. 13, 2019, named "SequenceListing.txt", created on May 29, 2019 (4.47 KB), is incorporated herein by reference.

TECHNICAL FIELD

The present disclosure relates to a peptide for inhibiting a TLR4 signaling pathway, a TLR4 antagonist including the peptide, and a composition for preventing or treating autoimmune diseases and inflammatory diseases. More specifically, the present disclosure relates to a peptide which binds to a TLR4/MD2 composite to inhibit the secretion of interleukin-6 (IL-6), NO, and ROS, and the activation of NFκB and MAPKs, a TLR4 antagonist including the peptide, and a composition for preventing or treating autoimmune diseases and inflammatory diseases.

BACKGROUND ART

Innate immunity is the first defense reaction against bacterial infections in a mammalian immune system, and pattern recognition receptors such as toll-like receptors (TLRs) are activated by recognizing pathogen-associated molecular patterns (PAMPs) or danger-associated molecular patterns (DAMPs).

TLRs play an important role in the innate immune response and are classified into extracellular TLRs acting on the plasma membrane, including TLR1, TLR2, TLR4, TLR5, TLR6, and TLR11 and intracellular TLRs acting in cells such as lysosomes or endosomes, including TLR3, TLR7, TLR8, and TLR9. Structurally, TLRs have a leucine-rich repeat (LRR) site at the N-terminus of the extracellular domain that is recognized by a ligand or an accessory molecule, and a Toll/interleukin 1 receptor (TIR) domain that transmits a signal at the intracellular C-terminus.

In particular, Toll-like receptor 4 (TLR4) is the first receptor identified in the TLR family, and activates innate immune signaling amplified through a process of MyD88 (myeloid differentiation 88)-dependent signaling pathways and MyD88-independent signaling pathways. Due to the role of TLR4, an interest in research to utilize TLR4 as a target for treating a variety of immune diseases is increasing. LPS recognized through accessory molecules such as LPS (lipopolysaccharide)-binding protein (LBP), CD 14 (cluster of differentiation 14) and MD2 (myeloid differentiation factor 2) activates TLR4. Activated TLR4 induces early activation of NFκB (nuclear factor kappa-light-chain-enhancer of activated B cells), the migration to a nucleus and activation of MAPKs (mitogen-activated protein kinases) through a process of Myd88-dependent signaling pathways. The activation of the NFκB and MAPKs secretes inflammatory cytokines such as TNF-α (tumor necrosis factor α), IL-1β (interleukin 1β) and IL-6 (interleukin 6). MyD88-independent signaling pathways are induced by the activation of TRAM/TRIF, interferon-regulatory factors (IRFs), and NFκB to secrete type 1 interferons. In addition, TLR4 induced by LPS produces oxidative stress substances such as nitrogen monoxide (hereinafter, referred to as NO) and active oxygen (hereinafter, referred to as ROS) in macrophages.

As such, TLR4 can be a target for treating various diseases such as autoimmune diseases, inflammatory diseases and cancer, and therefore, a substance targeting TLR4 and a medical composition for treating TLR4-related diseases are being studied. In particular, a large number of TLR4 promoters and antagonists were obtained by modifying the main skeletal structure of lipid A, and it has been revealed that eritoran, lipid A, and Rhodobactersphaeroids lipid A (RsLA) inhibit the interaction of LPS and MD2 and prevent LPS-induced shock in rats.

On the other hand, small peptides capable of acting similar or opposite to pathogen-associated molecular patterns (PAMPs) and interacting with target proteins are found through a variety of techniques, such as yeast two-hybrid assay and phage display, and studies are actively performed for these peptides in the field of therapeutic and vaccine adjuvants. Peptides are less susceptible to side effects than common therapeutic agents and are known to be susceptible to transformation, such as removing lipids or proteins from bacteria that activate TLRs.

However, there is a growing need for new antagonists that can effectively block the TLR4 signaling pathway and thereby treat the associated diseases.

DISCLOSURE

Technical Problem

The present inventors confirmed that the peptides of SEQ ID NOs: 1 to 3 inhibit the TLR4 signaling pathway induced by lipopolysaccharide (LPS) and inhibit the secretion of interleukin-6 (IL-6), NO, and ROS and the activation of NFκB and MAPKs, and then completed the present disclosure.

Accordingly, an object of the present disclosure is to provide a peptide represented by one or more amino acid sequences selected from the group consisting of SEQ ID NOs: 1 to 3, and a novel TLR4 antagonist including the same.

It is also an object of the present disclosure to provide a composition for preventing or treating autoimmune diseases including the peptide as an active ingredient.

It is also an object of the present disclosure to provide a composition for preventing or treating an inflammatory disease including the peptide as an active ingredient.

Technical Solution

In order to achieve the above object, the present disclosure provides a peptide represented by one or more amino acid sequences selected from the group consisting of SEQ ID NOs: 1 to 3.

The present disclosure also provides a TLR4 antagonist including a peptide represented by one or more amino acid sequences selected from the group consisting of SEQ ID NOs: 1 to 3.

The present disclosure also provides a composition for preventing or treating autoimmune diseases including a peptide represented by one or more amino acid sequences selected from the group consisting of SEQ ID NOs: 1 to 3 as an active ingredient.

The present disclosure also provides a composition for preventing or treating inflammatory diseases comprising a peptide represented by one or more amino acid sequences selected from the group consisting of SEQ ID NOs: 1 to 3 as an active ingredient.

Advantageous Effects

The peptide according to the present disclosure has an excellent effect of inhibiting the secretion of interleukin-6 (IL-6), NO, and ROS and the activation of NFκB and MAPKs by inhibiting a TLR4 signaling pathway induced by a lipopolysaccharide (LPS), and thus can be favorably used as a composition for preventing or treating autoimmune diseases and inflammatory diseases occurring by the TLR4 signaling pathway.

MODES OF THE INVENTION

Figure 1:
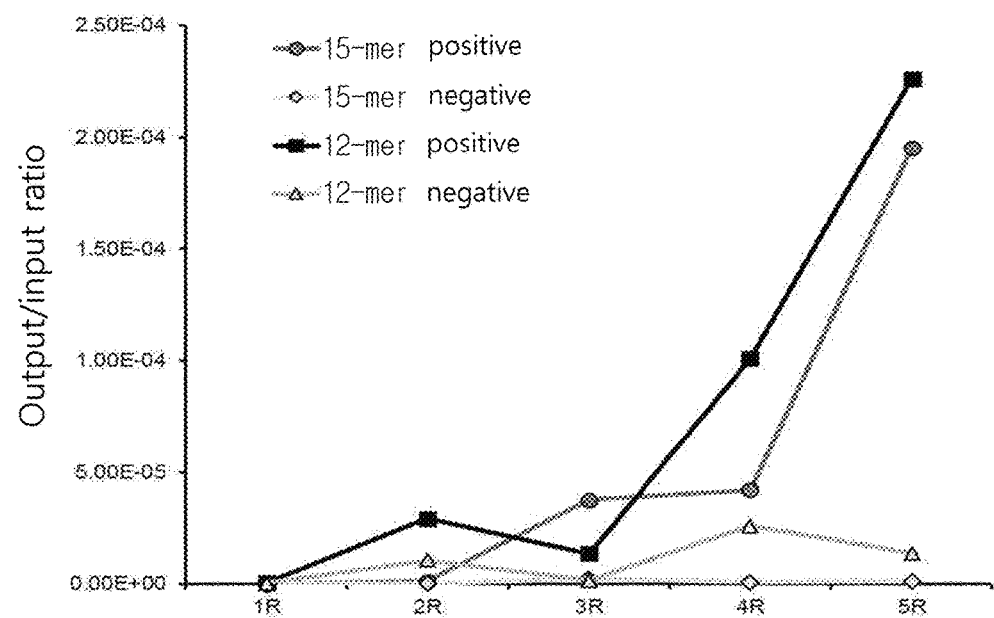
FIG. 1 is a graph illustrating the output/input ratio of each round of biopanning of the 15-mer and 12-mer peptide libraries to the recombinant human TLR4/MD2 composite (1 R to 5 R on the horizontal axis represents each round of biopanning).

Hereinafter, the present disclosure will be described in detail.

The present disclosure provides a peptide represented by one or more amino acid sequences selected from the group consisting of SEQ ID NOs: 1 to 3.

As used herein, the term "peptide" refers to a linear molecule formed by binding amino acid residues each other by peptide bonds. The peptide may be prepared according to a chemical synthesis method well known in the art, and may preferably be prepared according to a solid phase synthesis technique, but is not limited thereto.

As used herein, the term "TLR4" refers to a protein belonging to TLRs, which is a transmembrane protein family that functions as a monitor for pathogen infection, and is a protein encoded by the TLR4 gene, and is named as CD 284 (cluster of differentiation 284). The TLR4 is very important for the activation of the innate immune system because it recognizes a variety of pathogen-associated molecular patterns (PAMPs) including LPS of Gram-negative bacteria.

As used herein, the term "TLR4 signaling pathway" refers to a signaling pathway through TLR4 and may be an LPS response that is dependent on the TLR4/MD2 composite, which is a membrane-transverse composite formed by TLR4 and MD2 and through this, signals are transmitted. TLR4 transmits signals by many adapter proteins, and the signaling pathway works as Mal (also called TIRAP), MyD88, and TRAM and TRIF. The activated TLR4 activates NFκB through the Myd88-dependent signaling pathway to the nucleus and induces the activation of MAPKs. Inflammatory cytokines such as TNF-α, IL-1β and IL-6 are secreted by the activation of NFκB and MAPKs, and oxidative stress materials such as nitrogen monoxide (hereinafter, referred to as NO) and active oxygen (hereinafter, referred to as ROS) are generated in macrophages. In addition, activation of TRAM/TRIF, interferon-regulators (IRFs), and NFκB induces MyD88-independent signaling pathways and secretes type 1 interferon.

As used herein, the term "inhibition" refers to a phenomenon in which biological activity or vitality is decreased by deficiency, incongruity or many other causes, and the activity of TLR4 is partially or completely blocked, reduced, prevented, delayed, deactivated, or down-regulated.

As used herein, the term "TLR4/MD2 composite" refers to a membrane-transverse composite formed by TLR4 and MD2, and the peptides represented by SEQ ID NOs: 1 to 3 of the present disclosure bind TLR4/MD2 composite, and thus can inhibit a TLR4 signaling pathway.

Accordingly, the present disclosure provides a TLR4 signaling pathway inhibiting use of the peptides represented by SEQ ID NOs: 1 to 3.

The "one or more peptides selected from the group consisting of SEQ ID NOs: 1 to 3" of the present disclosure means a peptide having the same sequence as the sequence of SEQ ID NOs: 1 to 3 as long as it has an ability to be bound effectively to the TLR4/MD2 composite. The peptides may include a peptide substituted by a conservative substitution of an amino acid and a peptide having 70% or more, preferably 80% or more, and more preferably 90% or more of sequence homology with the peptide. The term "homology" refers to a wild type amino acid sequence and a similar degree to a wild type nucleic acid sequence.

According to one embodiment of the present disclosure, the peptides represented by SEQ ID NOs: 1 to 3 of the present disclosure inhibit a TLR4 signaling pathway induced by lipopolysaccharide (LPS), thereby producing an excellent effect of inhibiting the secretion of interleukin-6 (IL-6), NO, and ROS, and the activation of NFκB and MAPKs, and thus can be favorably used as a composition for preventing or treating autoimmune diseases and inflammatory diseases occurring by the TLR4 signaling pathway.

The present disclosure also provides a TLR4 antagonist including the peptide.

As used herein, the term "antagonist" means a molecule that partially or completely inhibits the effects of other molecules such as receptors or intracellular mediators, by any mechanism.

As used herein, the term "TLR4 antagonist" refers to a substance that can directly, indirectly, or substantially interfere with, reduce or inhibit the biological activity of TLR4, preferably a peptide reactive with TLR4 refers to a substance capable of directly binding to TLR4 or TLR4/MD2 composite, blocking the TLR4 signaling pathway by neutralizing the activity of TLR4 and inducing the reduction in the activation of NFκB and MAPKs, thereby reducing the secretion of inflammatory cytokines, NO, and ROS.

Accordingly, the present disclosure provides a composition for preventing or treating an autoimmune disease including the peptide as an active ingredient.

As used herein, the term "autoimmune disease" refers to a disease caused by a process in which a problem occurs in inducing or maintaining self-tolerance and an immune response to a self-antigen occurs, thereby attacking the own tissue. The term "self tolerance" refers to immunologic unresponsiveness that does not react harmful to an antigenic substance constituting self. The autoimmune diseases of the present disclosure include insulin-dependent diabetes, multiple sclerosis, experimental autoimmune encephalomyelitis, rheumatoid arthritis, experimental autoimmune arthritis, myasthenia gravis, thyroiditis, experimental uveitis, Hashimoto's thyroiditis, primary myxedema, thyrotoxicosis, malignant anemia, autoimmune atrophic gastritis, Addison's disease, early menopause, male infertility, juvenile diabetes, Goodpasture syndrome, pemphigus vulgaris, pemphigoid, sympathetic ophthalmia, lens-induced uveitis, autoimmune hemolytic anemia, idiopathic leukopenia, primary biliary cirrhosis, chronic active hepatitis Hbs-ve, latent cirrhosis, ulcerative colitis, Sjogren's syndrome, scleroderma, Wegener's granulomatosis, polymyositis/dermatomyositis, discoid LE and systemic lupus erythematosus, but are not limited thereto.

The composition for the prevention or treatment of autoimmune diseases of the present disclosure may include a pharmaceutically effective amount of the peptide alone or may include one or more pharmaceutically acceptable carriers, excipients, or diluents. A pharmaceutically effective amount as used herein refers to an amount sufficient to prevent, ameliorate, and treat symptoms of autoimmune diseases.

The term "pharmaceutically acceptable" as used herein refers to a composition that is physiologically acceptable and does not normally cause an allergic reaction such as gastrointestinal disorder, dizziness, or the like when administered to a human. Examples of the carrier, excipient, and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, water, methylhydroxybenzoate, propylhydroxybenzoate, talc, magnesium stearate, and mineral oil. It may further include fillers, anti-coagulants, lubricants, wetting agents, perfumes, emulsifiers, and preservatives, etc.

In addition, the composition of the present disclosure may include one or more known active ingredients having an effect of treating an autoimmune disease together with the peptide.

The composition of the present disclosure may be formulated using methods known in the art so as to provide rapid, sustained or delayed release of the active ingredient after administration to a mammal other than a human. The formulations may be in the form of powders, granules, tablets, emulsions, syrups, aerosols, soft or hard gelatin capsules, sterile injectable solutions, sterile powders.

The composition of the present disclosure may be administered through various routes including oral, transdermal, subcutaneous, intravenous or muscular, and the dosage of the active ingredient may be suitably selected according to various factors such as the route of administration, the age, sex, weight, and severity of a patient. The composition for preventing or treating an autoimmune disease according to the present disclosure may be administered in combination with a known compound having an effect of preventing, ameliorating or treating symptoms of an autoimmune disease.

The present disclosure also provides a composition for preventing or treating inflammatory diseases including the peptide as an active ingredient.

In the present disclosure, the term "inflammatory disease" refers to a disease caused by inflammatory substances (inflammatory cytokines) such as TNF-α, IL-1, IL-6, prostaglandin, leukotriene or NO secreted in immune cells such as macrophages by excessive acceleration of the immune system due to harmful stimuli such as an inflammatory inducer or radiation. The inflammatory diseases of the present disclosure include asthma, eczema, psoriasis, allergies, rheumatoid arthritis, psoriatic arthritis, contact dermatitis, atopic dermatitis, acne, atopic rhinitis, allergic dermatitis, chronic sinusitis, seborrheic dermatitis, gastritis, gout, gouty arthritis, ulcers, chronic bronchitis, pulmonary inflammation, Crohn's disease, ulcerative colitis, ankylosing spondylitis, sepsis, vasculitis, bursitis, lupus, rheumatoid multiple myalgia, temporal arteritis, multiple sclerosis, solid cancer, Alzheimer's disease, arteriosclerosis, obesity, and virus infection, but are not limited thereto.

Since the composition for preventing or treating the inflammatory disease includes a pharmaceutical preparation including the above-mentioned peptide as an active ingredient, the contents overlapping with the composition of the present disclosure described above are omitted by the description of the overlapping contents in order to avoid excessive complexity.

The present disclosure also provides a method for preventing or treating an autoimmune disease, in which the method includes: administering to a subject a peptide represented by one or more amino acid sequences selected from the group consisting of SEQ ID NOs: 1 to 3.

The present disclosure also provides a method for preventing or treating an inflammatory disease, in which the method includes: administering to a subject a peptide represented by one or more amino acid sequences selected from the group consisting of SEQ ID NOs: 1 to 3.

Hereinafter, the present disclosure will be described more specifically with reference to examples and experimental examples. The following examples and experimental examples are merely illustrative of the present disclosure, and the content of the present disclosure is not limited by the following examples and experimental examples.

Example 1: Screening for TLR4/MD2 Specific Peptides

In order to screen for peptides that specifically bind to the TLR4/MD2 composite, 15-mer peptide constructed fUSE55, and 12-mer peptide constructed a pHEN2 phage display library, and a phage display method was performed.

Example 1-1: Preparation of Library

First, in order to prepare a 15-mer peptide library, a forward primer 5'-TTG ATC GCA AGG ATC GGC TAG C-3' (SEQ ID NO: 4) reverse primer 5'-AA GGC CTT GGT ACC GCT GCC ACC (MNN)$_{15}$ GCT AGC CGA TCC TTG CGA TCA A-3' (SEQ ID NO: 5) and Pfu DNA polymerase (SolGent, Daejeon, Korea) were used, and the processes of denaturalizing at 90° C. for 30 seconds, annealing at 55° C. for 30 seconds, and extending at 72° C. for 60 seconds were repeated 25 times to amplify DNA. The amplified DNA strands were cut with NheI/KpnI and ligated into a fUSE55 vector using T4 DNA ligase (New England Biolabs, Inc., Ipswich, Mass., USA). Three DNA libraries were transferred into DH10B strains, which are electrocompetent $E.$ $coli$, resulting in $6.6 \times 10^7$ clones, then amplified and propagated in $E.$ $coli$ strain TG-1.

In addition, in order to prepare and insert a random 12-mer peptide library into the pill region of pHEN2, the forward primer 5'-GCC CAG CCG GCC ATG GCC (NNK)$_{12}$ TCG AGT GGT GGA GGC GGT TCA G-3' (SEQ ID NO: 6) reverse primer 5'-GCC AGC ATT CAC AGG AGG TTG AG-3' (SEQ ID NO: 7) and Pfu DNA polymerase were used, and the processes of the above conditions were repeated 25 times to perform three independent PCRs. The resulting product of PCR was cut with NheI/KpnI, ligated into a pHEN2 vector using T4 DNA ligase, and the library DNAs were introduced into XL-1 Blue (Stratagene, Santa Clara, Calif., USA) strains, which are electrocompetent $E.$ $coli$ cells. The phage particles were prepared to have a variety of $2.0 \times 10^9$ clones using a hyperphage M13K07Δ pIII (PROGEn Biotechnik GmbH, Heidelberg, Germany), followed by amplification in $E.$ $coli$ strain XL-1.

Example 1-2: Biopanning

Biopanning was performed on a modified Griffin-1 library (Griffin H., MRC, Cambridge, UK, unpublished data). More specifically, TLR4/MD2 composite (R&D Systems, Inc., Minneapolis, Minn., USA) 5 µg/ml of resuspended recombinant human in a coated buffer was coated with Nunc Maxisorp 96-well plate (Thermo Fisher Scientific Inc., Waltham, Mass., USA) and then refrigerated overnight. Then, the cells were blocked with 1% BSA in PBS for 2 hours at room temperature, and then the refrigerated wells were exposed to a phage library for 2 hours at room temperature so that the BSA concentration would become 1% in PSB (PBST) including the final concentration 0.05% Tween 20. The phages bound to the library were dissolved in 100 µl of elution buffer (100 mM HCl), separated, washed with PBST and neutralized to ⅛ volume of 1M Tris HCl at pH 11. The phage titer for 15-mer library was calculated in $E.$ $coli$ TG1 above an LB (Luria-Bertani) agar plate including 200 µg/ml of tetracycline (Tet) and 10 µg/ml of ampicillin (Amp), and that for the 12-mer library was calculated as CFU in XL-1 Blue on the $E.$ $coli$ agar plate. The phage was then amplified in $E.$ $coli$ TG1, X11 Blue and purified during subsequent rounds of panning through PEG (polyethylene0glycol)/NaCl precipitation. In each round of a total 5 rounds, the input-output ratio was calculated by measuring the concentration efficiency, and the results thereof are illustrated in FIG. 1.

As illustrated in FIG. 1, the output/input ratio for the recombinant human TLR4/MD2 composite of the 15-mer and 12-mer positive peptide library was further increased as it goes through several rounds. Therefrom, it can be understood that the efficiency of biopanning of five rounds according to the present disclosure is excellent.

Example 1-3: Phage Screening Showing High Binding Affinity for the TLR4/MD2 Composite Separate independent clones of the infected cells in Examples 1-2 above were collected in LB/Tet of the 15-mer library and U-bottom 96-well plates in the LB/Amp agar plate of the 12-mer library. Then, it was nurtured overnight at 37° C. after five rounds of bio-panning, placed on LB/Tet or LB/Amp agar plates, and centrifuged at 3000 g for 30 minutes to obtain a supernatant phage preparation. In order to measure the phage-binding affinity, the supernatant, which was mixed with the same volume of a binding buffer including 2% BSA in PBS, was added to 1.25 µg/ml of TLR4/MD2-positive 96-well plate and TLR4/MD2-negative 96-well plate. The wells were blocked with blocking buffer (PBST including 2% BSA) for 2 hours and then washed with PBS. After binding reaction at room temperature for 1 hour, the unbound phage was removed by washing with PBST. The combined phages were cultured with 100 µl of anti-M13 antibody conjugated to HRP (horseradish peroxidase), the unbound remaining phases were washed with PBST and removed to detect the combined phages. Thereafter, 100 µl of tetramethylbenzidine (Thermo Fisher Scientific Inc.) was added to each well, and then the mixture was allowed to stand at room temperature until color change appeared, and then 100 µl of 1N $H_3PO_4$ was added to stop the reaction. The phage showing high binding affinity was selected by measuring the absorbance at 450 nm using ELISA (BioTek Instruments, Inc., Winooski, Vt., USA) and the selected phages were used in the following experiments.

Example 2: DNA Sequencing and TAPs Synthesis

In order to isolate the phage DNA from the phage selected in Example 1-3 above, a Miniprerp Kit (GeneAll Biotechnology, Seoul, Korea) was used. The 15-mer DNA used a primer having a nucleotide sequence of 5'-TGA ATT TCC TGT ATG AGG-3' (SEQ ID NO: 8) and the 12-mer DNA used a primer having a nucleotide sequence of 5'-TTG TGA GCG GAT AAC AAT TTG-3' (SEQ ID NO: 9) to perform DNA sequencing with Macrogen (Macrogen Inc., Seoul, Korea). DNA sequences identified through the sequencing were translated into amino acid sequences and mutations were measured using BioEdit software and sorted. Then, peptides (TAPs; TLR4 agonistic peptides are generically referred to as TAP1, TAP2, and TAP3, hereinafter referred to as TAPs) having the amino acid sequence illustrated in Table 1 having high binding affinity to TLR4/MD2 were synthesized in PEPTRON (Daejeon, Korea) so as to have purity of 95% or higher. TAP1 was dissolved in water so that the final concentration would be 10 mg/ml, and TAP2 and TAP3 were dissolved in dimethylsulfoxide, and then were appropriately aliquoted at −20° C. for storage.

TABLE 1

Peptides that specifically bind to TLR4/MD2

| Names | Peptide sequences |
|---|---|
| TAP1 (SEQ ID NO.: 1) | AS<u>ANKNLLFKIRYSTAR</u>GGS |
| TAP2 (SEQ ID NO.: 2) | AM<u>ALDCFRWGWRMW</u>CSSG |
| TAP3 (SEQ ID NO.: 3) | AM<u>AYEIRCWWRWCY</u>TSSG |

The sequences revealed by biopanning are underlined.

Example 3: Cell Culture and Preparation

HEK-Blue™ hTMR4 cells (InvivoGen, San Diego, Calif., USA) was added to DMEM (Dulbecco's modified Eagle's medium) (Thermo Fisher Scientific Inc.) to which 10% of fetal bovine serum (FBS) (Thermo Fisher Scientific Inc.), 50 IU/ml of penicillin, 50 μg/ml of streptomycin (Thermo Fisher Scientific Inc.), 100 mg/ml of normocin (InvivoGen) and an HEK-Blue mixture of antibiotics (2 ml per 500 ml) (InvivoGen) are added, and were cultured in a culture system of a humidified condition of 5% $CO_2$, 37° C. Mouse macrophage RAW264.7 cells (ATCC, Manassas, Va., USA) were put in Low-Glucose DMEM (Thermo Fisher Scientific Inc.) to which 10% of FSB, 100 IU/ml of penicillin and 100 μg/ml of streptomycin are added, and were cultured in a culture system. LPS was purchased from Sigma-Aldrich Co. (St. Louis, Mo., USA) and $PAM_3CSK_4$ was purchased from InvivogGen.

Experimental Example 1: Confirmation of TLR4/MD2-Binding Affinity of TAPs

In order to confirm the TLR4/MD2-binding affinity of TAPs (TAP1, TAP2, TAP3), the activity of NFκB was measured in HEK-Blue™ hTLR4 cells cultured in Example 3 above. The inductive secreted embryonic alkaline phosphatase (SEAP) reporter gene was located below the regulatory portion of the IL-12 p40 minimal promoter (where IL-12 p40 is produced by activation of NFκB and AP-1 after stimulation of TLR4), which includes a site of DNA binding of NFκB and AP-1 (activator protein 1). Thereafter, HEK-Blue™ hTLR4 cells were treated by varying concentrations of TAPs at 10, 50, and 100 μg/ml, and the average value of SEAP activity was calculated to measure the activity of TLR4. The results thereof are illustrated in FIG. 2.

Figure 2:
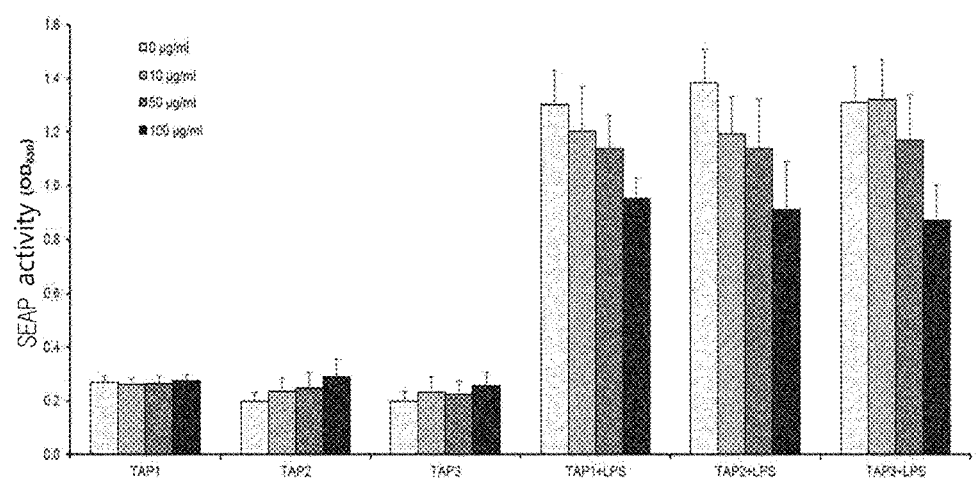
FIG. 2 is a graph illustrating SEAP activity when TAPs (TAP1, TAP2, and TAP3) or TAPs and LPS are treated together at different concentrations in HEK-Blue™ hTLR4 cells.

As illustrated in FIG. 2, SEAP activity was not significantly changed when only TAPs were added, but when TLR4 was stimulated with LPS after TAPs treatment, LPS-induced SEAP activity decreased in a concentration-dependent manner. Therefrom, it can be understood that the TAPs of the present disclosure act as TLR4/MD2 antagonists and effectively inhibit the activity of NFκB induced by LPS.

Experimental Example 2: Effect of TAPs on IL-6 and NO Secretion and ROS Generation In order to confirm whether the secretion of IL-6 (interleukin-6) and NO (nitric oxide) and the generation of ROS (reactive oxygen species) in the cytoplasm and nucleus are inhibited when the TAPs prepared in Example 2 above were treated with mouse macrophage RAW264.7 cells cultured in Example 3 above, the following experiments were conducted.

Experimental Example 2-1: Effect of TAPs on IL-6 and NO Secretion

IL-6, NO numerical values of the culture supernatant of RAW264.7 cells of Example 3 above treated with the TAPs prepared in Example 2 above were measured using a mouse IL-6 ELISA kit Ready-SET-Go! (eBioscience San Diego, Calif., USA) and NO detection kit (iNtRON Biotechnology, Gyeonggi, Korea). Microplate Reader Spectrophotometer (Molecular Devices In.) was used to measure absorbance at 450 nm for IL-6 and 540 nm for NO, and the results were analyzed using Soft Max Pro 5.3 software (Molecular Devices Inc.). The results thereof are illustrated in FIGS. 3 and 4.

Figure 3:
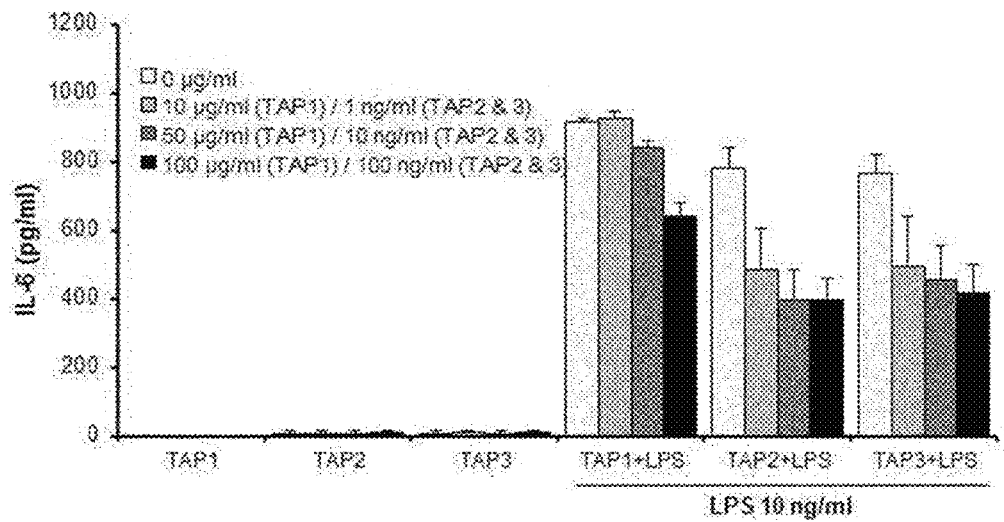
FIG. 3 is a graph illustrating the amount of IL-6 secreted when TAPs or TAPs and LPS were treated together in RAW264.7 cells, which are mouse macrophages, at different concentrations.
Figure 4:
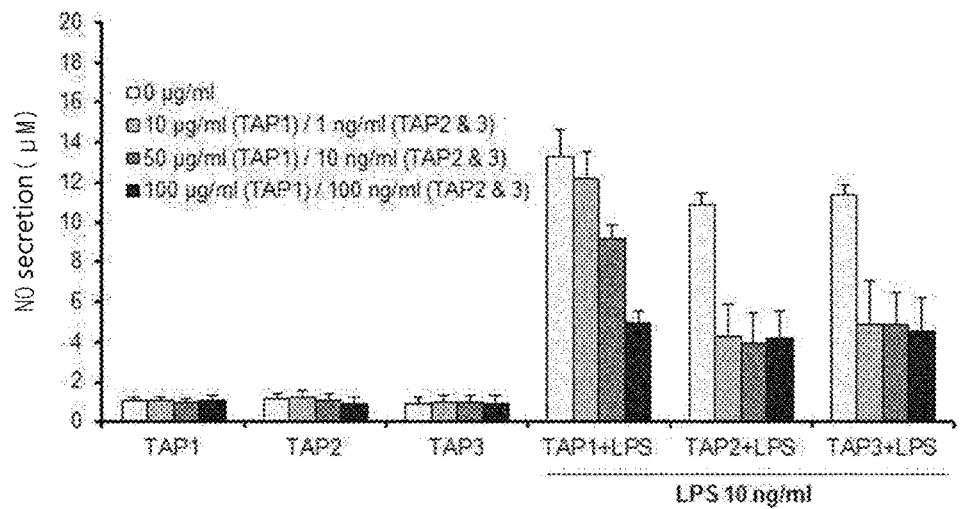
FIG. 4 is a graph illustrating the amount of NO secreted when TAPs or TAPs and LPS were treated together in RAW264.7 cells, which are mouse macrophages, at different concentrations.

As illustrated in FIGS. 3 and 4, there was no significant change in the secretion amount of IL-6 and NO when only TAPs were added, but it was confirmed that when TAPs and LPS were treated together, the secretion amount of IL-6 and NO decreased. Therefrom, it can be understood that TAPs according to the present disclosure inhibit the secretion of IL-6 and NO induced by LPS.

Experimental Example 2-2: Western Blotting of iNOS (Inducible Nitric Oxide Synthase)

In order to perform Western blotting, a pre-protein extraction solution (M-PER, Thermo Fisher Scientific Inc.) was mixed with the protease and phosphatase inhibitory mixture, and was added to the RAW264.7 cell pellet of Example 3 above. The pellet was cooled for 10 minutes and then the lysate was centrifuged at 16000×g for 10 minutes. Then, NE-PER nuclear and cytoplasmic extraction reagents (Thermo Fisher Scientific Inc.) was used to extract the cytoplasmic and nuclear proteins, respectively, and the concentration of the protein was measured using a BCA kit (Sigma-Alderich Co. LLC). The same amount of protein was then developed on SDS-polyacrylamide gel and transferred to Hybond-ECL nitrocellulose membrane (Amersham Pharmacia Biotech, Inc., Piscataway, N.J., USA). The membrane was blocked with 0.05% nonfat dry milk in deionized water for 1 hour and immunoblotted with the primary antibody by gently shaking overnight at a temperature of 4° C. (The primary antibody was the antibody for iNOS (BD Biosciences, San Jose, Calif., USA) and β-actin (Santa Cruz Biotechnology, Inc., Dallas, Tex., USA)). The membrane was then shaken thoroughly with PBST and then the membrane was cultured with anti-mouse/-rabbit HRP-conjugated secondary antibody (Thermo Fisher Scientific Inc.) for 2 hours, and the protein was detected with SuperSignal West Pico ECL solution (Thermo Fisher Scientific Inc.) and was visualized with a Fuji LAS-3000 system (Fujifilm, Tokyo, Japan). The results thereof are illustrated in FIG. 5.

Figure 5:
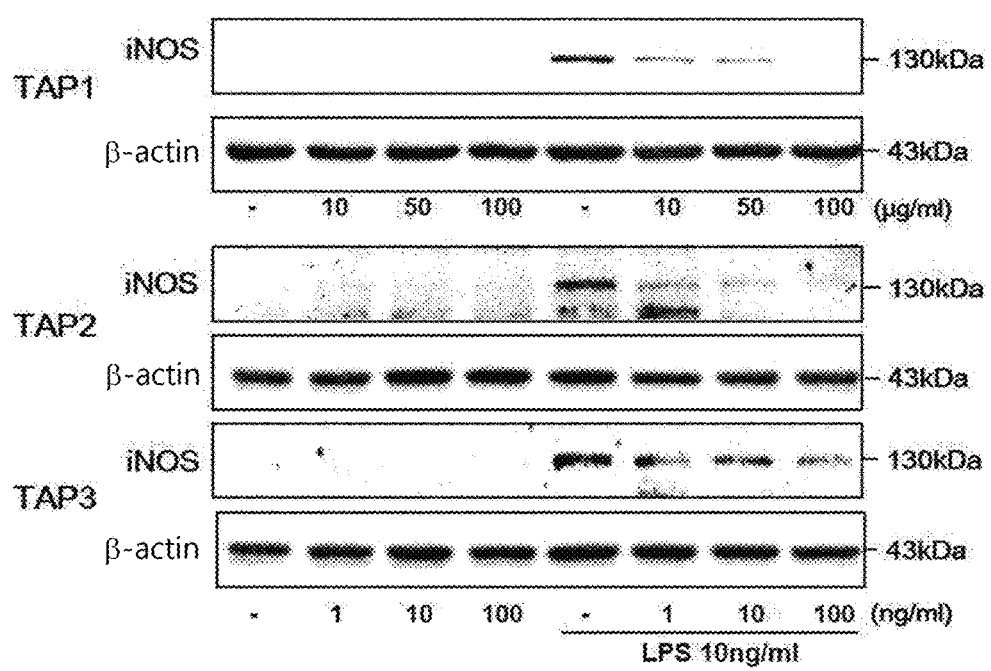
FIG. 5 is a graph illustrating the results of confirming the expression amount of iNOS through western blotting when TAPs or TAPs and LPS were treated together in RAW264.7 cells, which are mouse macrophages, at different concentrations.

As illustrated in FIG. 5, when the LPS was added, the expression of iNOS was increased as compared with the control group of β-actin. However, when the TAPs were treated together, the expression of iNOS decreased in a concentration-dependent manner. Therefrom, it can be understood that the TAPs according to the present disclosure inhibit the expression of iNOS induced by LPS.

Experimental Example 2-3: Effect of TAPs on NO and ROS Generation

In order to confirm the effect of the TAPs prepared in Example 2 above on the generation of NO and ROS (reactive oxygen species) in the cytoplasm, RAW264.7 cells, which are the mouse macrophages cultured in Example 3 above, were treated with TAPs. Each of them is strained with DAF-FM (Invitrogen Corp., CA, USA), DCF-DA (Invitrogen Corp.) and MitoSOX (Invitrogen Corp.), and then cultured for 1 hour. Then, centrifugation was performed at 200×g for 5 minutes, collected and transferred to a brown tube, and stored at a temperature of 4° C. in PBS. NO was quantified with DAF-FM staining, cytoplasmic ROS was quantified with DCF-DA staining, and ROS of mitochondria was quantified with MitoSOX staining. The intensity of the DAF-FM, DCF-DA and MitoSOX fluorescent materials was measured using FACSAria III as diva software, and the quantification was performed. Images were obtained using WinMDI software, and the results thereof are illustrated in FIGS. 6 to 8.

Figure 6:
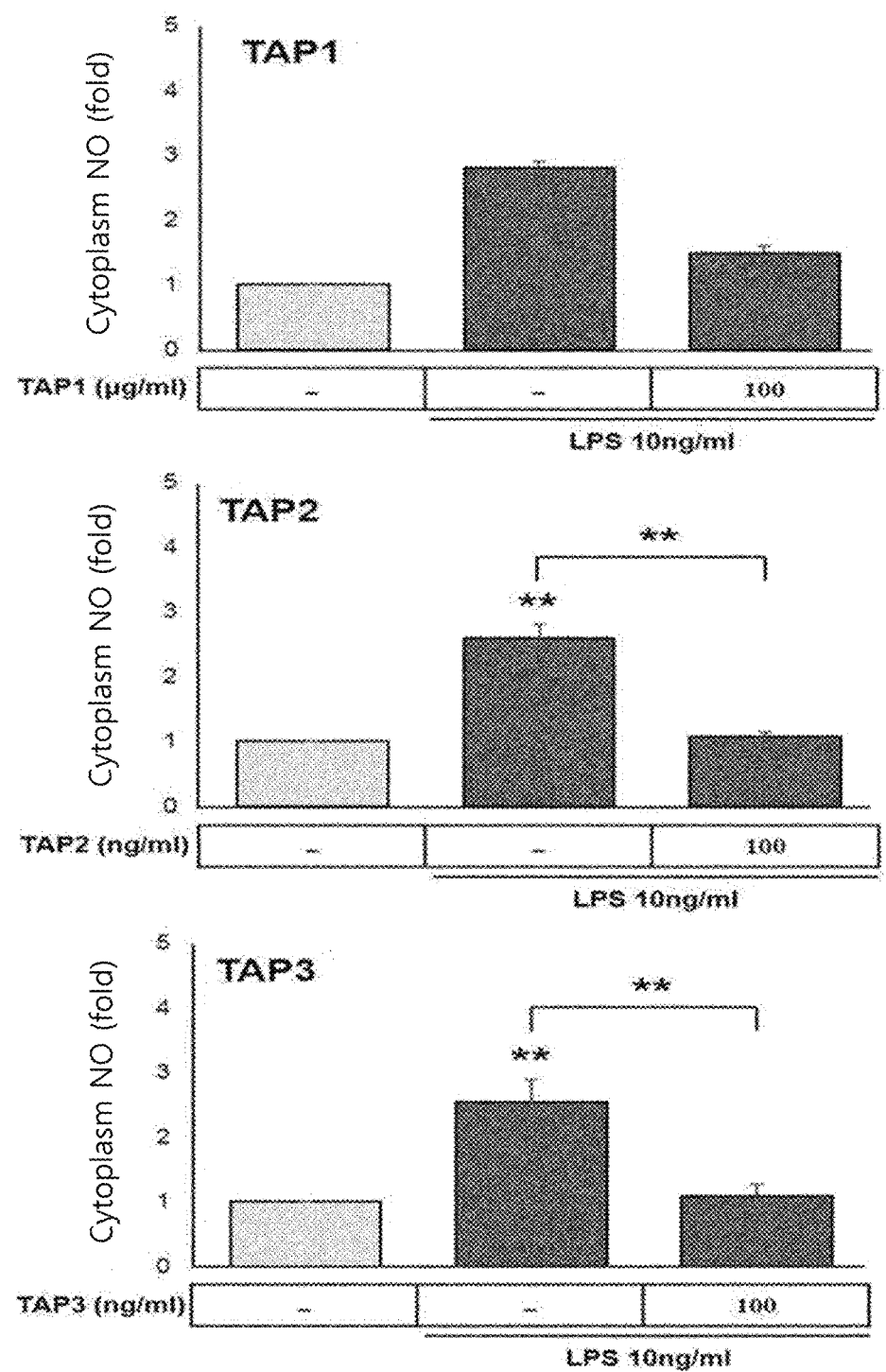
FIG. 6 is a graph illustrating the amount of NO generated in the cytoplasm when TAPs or TAPs and LPS are treated together in RAW264.7 cells, which are mouse macrophages.
Figure 7:
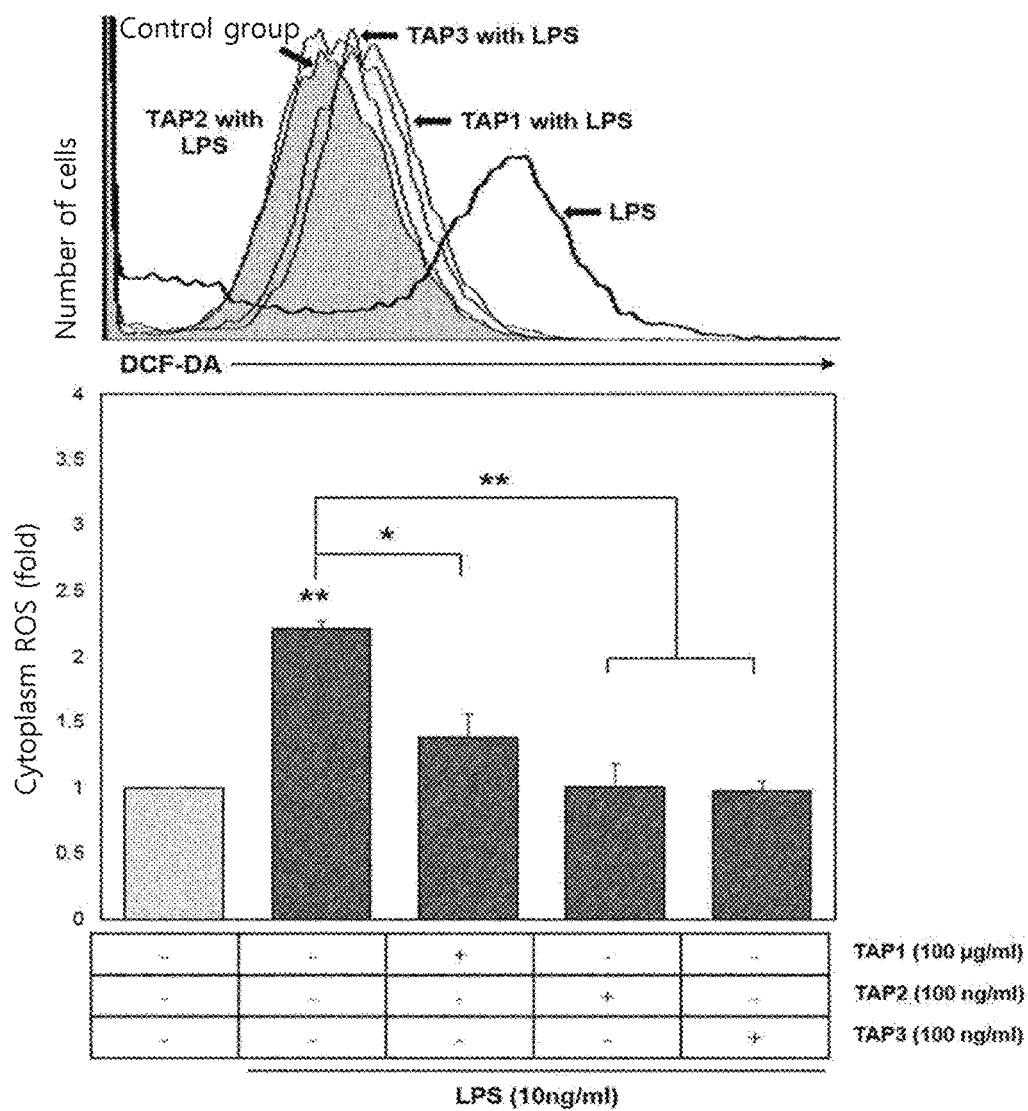
FIG. 7 is a graph illustrating the number of cells stained with DCF-DA and the amount of ROS generated in the cytoplasm when TAPs or TAPs and LPS are treated together in RAW264.7 cells, which are mouse macrophages.
Figure 8:
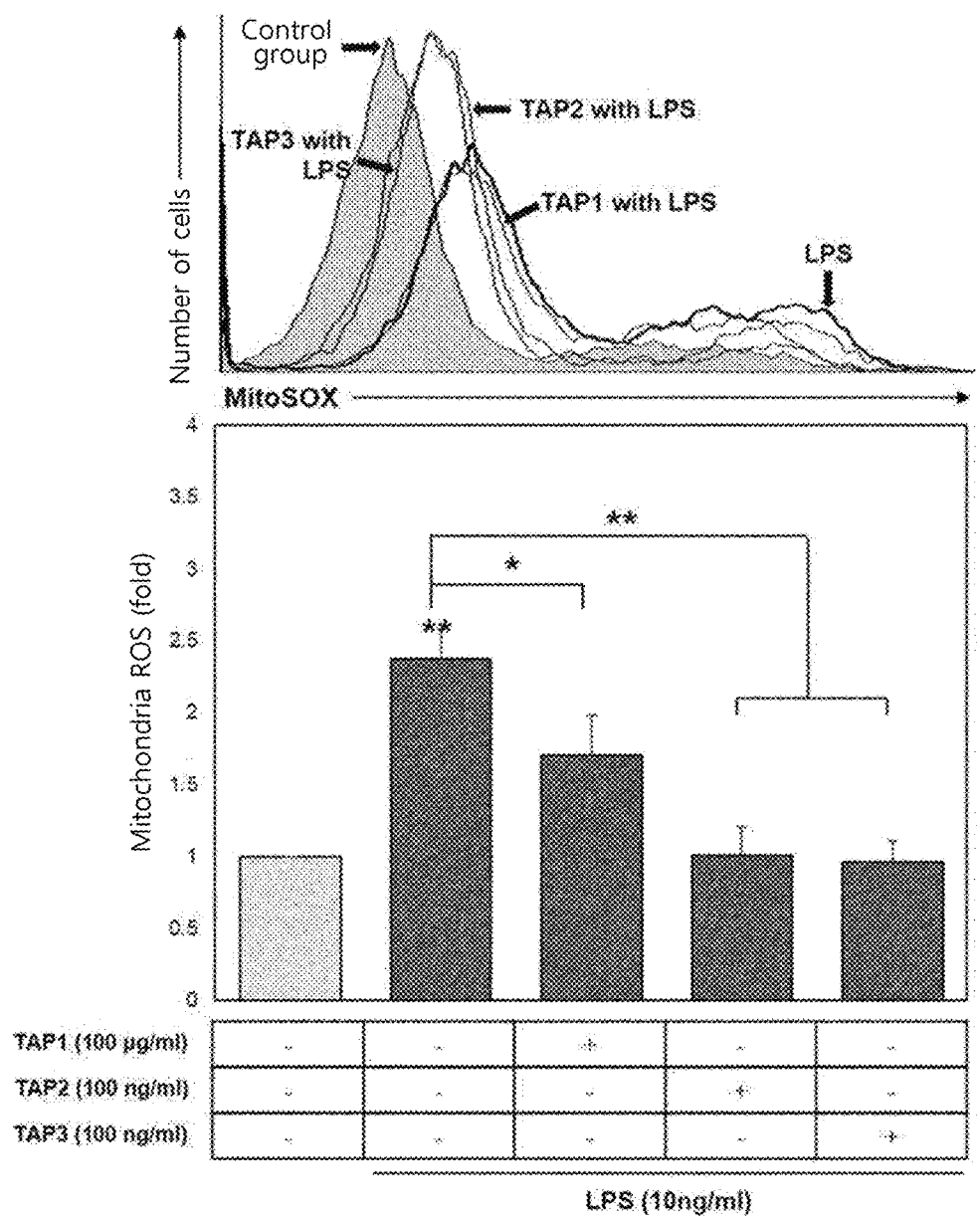
FIG. 8 is a graph illustrating the number of cells stained with MitoSOX and the amount of ROS generated in mitochondria when TAPs or TAPs and LPS are treated together in RAW264.7 cells, which are mouse macrophages.

As illustrated in FIGS. 6 to 8, when LPS was added, the generation degree of NO and ROS in the cytoplasm and ROS in the nucleus was increased. However, when TAPs were treated together, the generation degree of NO and ROS was decreased in a concentration-dependent manner. Therefrom, it can be understood that the TAPs according to the present disclosure inhibit the generation of NO and ROS induced by LPS in the cytoplasm and nucleus.

Experimental Example 3: Effect of TAPs on the Activity of NFκB and MAPKs

The following experiment was conducted to confirm the effect of the TAPs prepared in Example 2 above on the activity of NFκB and MAPKs.

Experimental Example 3-1: Western Blotting of NFκB and MAPKs

Western blotting was performed in the same manner as in Experimental Example 2-2 to confirm the effect of the TAPs prepared in Example 2 above on the activity of NFκB and MAPKs. The primary antibodies used were the antibodies for HDAC1 (Merck Millipore, Billerica, Mass., USA), NFκB (p65), IκBα, p-ERK, ERK, p-JNK, JNK, p-p38, p38, ATF3 and β-actin (Santa Cruz Biotechnology, Inc., Dallas, Tex., USA) and the secondary antibody was an anti-rat/-rabbit HRP-conjugated secondary antibody (Thermo Fisher Scientific Inc.). The results obtained by performing Western blotting are illustrated in FIGS. 9 and 10.

Figure 9:
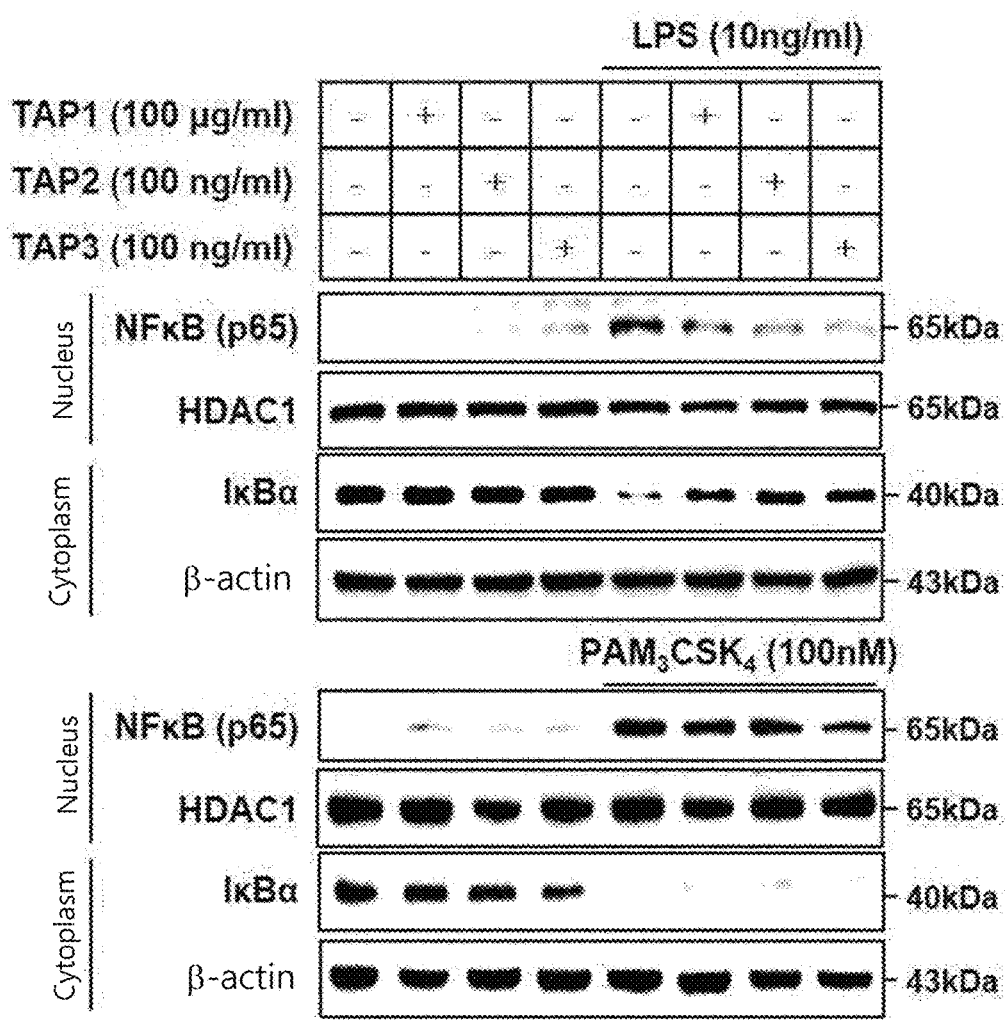
FIG. 9 is a graph illustrating the results of confirming the activity of NFκB through western blotting when TAPs or TAPs with LPS or TAPs and PAM$_3$CSK$_4$ are treated in RAW264.7 cells, which are mouse macrophages.

As illustrated in FIG. 9, when only LPS was treated in mouse macrophage RAW264.7 cells, which is a control group, the activity of NFκB was increased and IκBα was degraded, but when TAPs were treated together, the activity of NFκB was inhibited and the degree of degradation of IκBα was decreased. In particular, when $PAM_3CSK_4$, which is a TLR1/2 ligand, was treated with TAPs, there was no effect on the activity of NFκB and the degree of degradation of IκBα. Therefrom, it can be understood that the TAPs according to the present disclosure specifically bind to TLR4 and inhibit the activity of NFκB induced by LPS.

Figure 10:
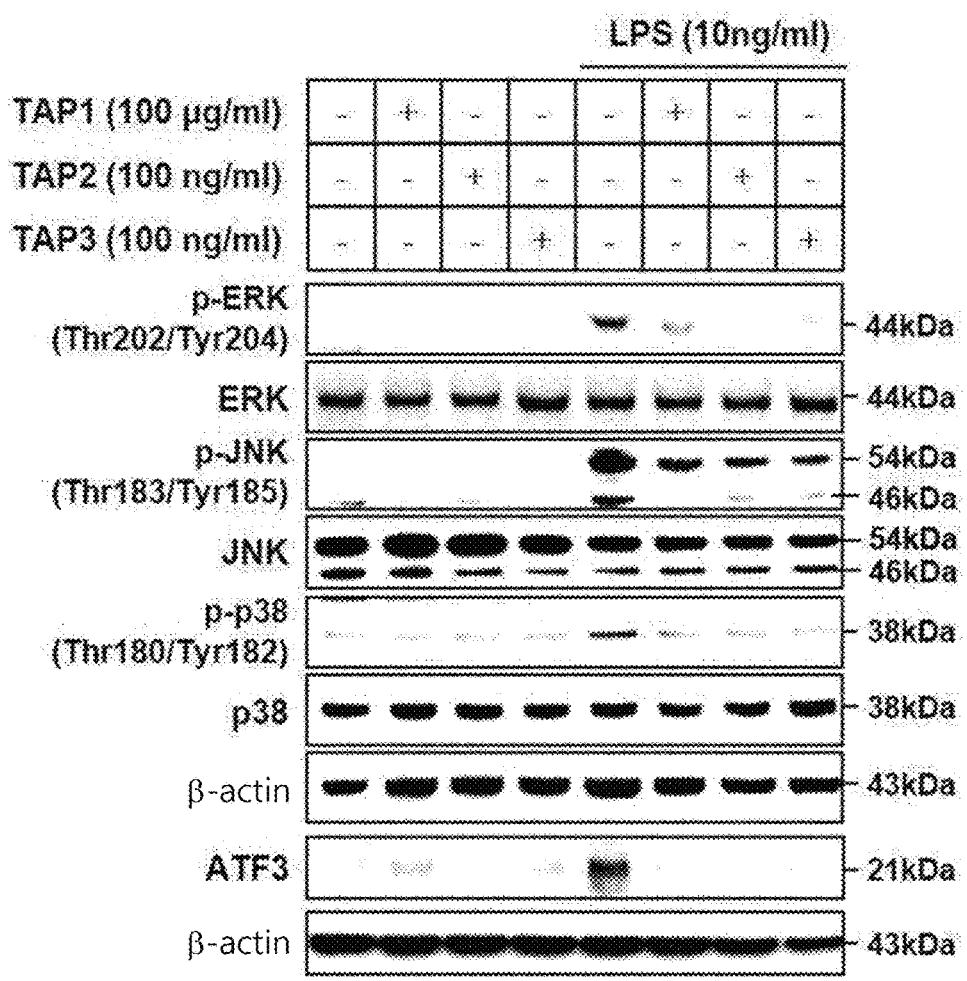
FIG. 10 is a graph illustrating the results of confirming the degree of phosphorylation of ERK, JNK, and p38 and the expression level of ATF3 through western blotting in order to examine the activity of MAPKs when TAPs or TAPs and LPS are treated together in RAW264.7 cells, which are mouse macrophages.

In addition, as illustrated in FIG. 10, when only LPS was treated in mouse macrophage RAW264.7 cells, which is a control group, the activity of MAPKs was increased, ERK, JNK and p38 were phosphorylated, and ATF3 expression was increased, but when TAPs were treated together, the activity of MAPKs was inhibited, the degree of phosphorylation of the enzymes was decreased, and the amount of ATF3 expression was also decreased. Therefrom, it can be understood that the TAPs according to the present disclosure inhibit the activity of MAPKs induced by LPS and ATF3 expression.

Experimental Example 3-2: Confirmation of Movement of NFκB to the Nucleus

HEK-Blue™ hTLR4 cells cultured in Example 3 above were seeded in a 96-well plate of $10^4$/well and grown in an incubator for 2 days. After exchanging the supernatant, the cells in the incubator were treated with each TAPs and after 1 hour, 20 μg/ml of LPS was treated, respectively. The HEK-Blue™ hTLR4 cells were then fixed with 3.7% formaldehyde for 10 minutes, immersed in 0.2% Triton X-100 for 15 minutes and then blocked with 5.0% FBS for 1 hour. The blocked cells were cultured with primary antibody for 1 hour and then cultured with AlexaFluor 546-conjugated secondary antibody (Invitrogen Corp.) for 1 hour. Thereafter, 5 μM of Hoechst 33258 (Sigma-Aldrich Co.) was used to strain at room temperature for 30 minutes, and a confocal microscope (LSM-700, Carl Zeiss MicroImaging GmbH, Jena, Germany) was used to count the number of the fluorescently stained cells. Images were analyzed using Zen 2009 software (Carl Zeiss MicroImaging GmbH). The results thereof are illustrated in FIG. 11.

Figure 11:
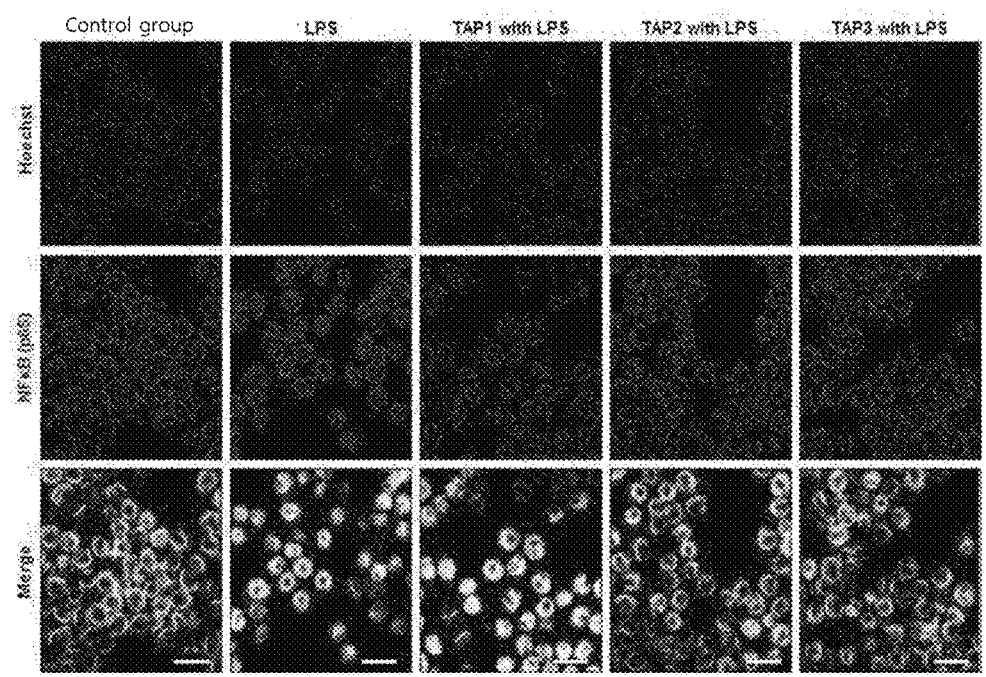
FIG. 11 is a graph illustrating the results of confirming whether NFκB is transferred from the cytoplasm to the nucleus when LPS or TAPs and LPS are treated together in HEK-Blue™ hTLR4 cells.
Figure 12:
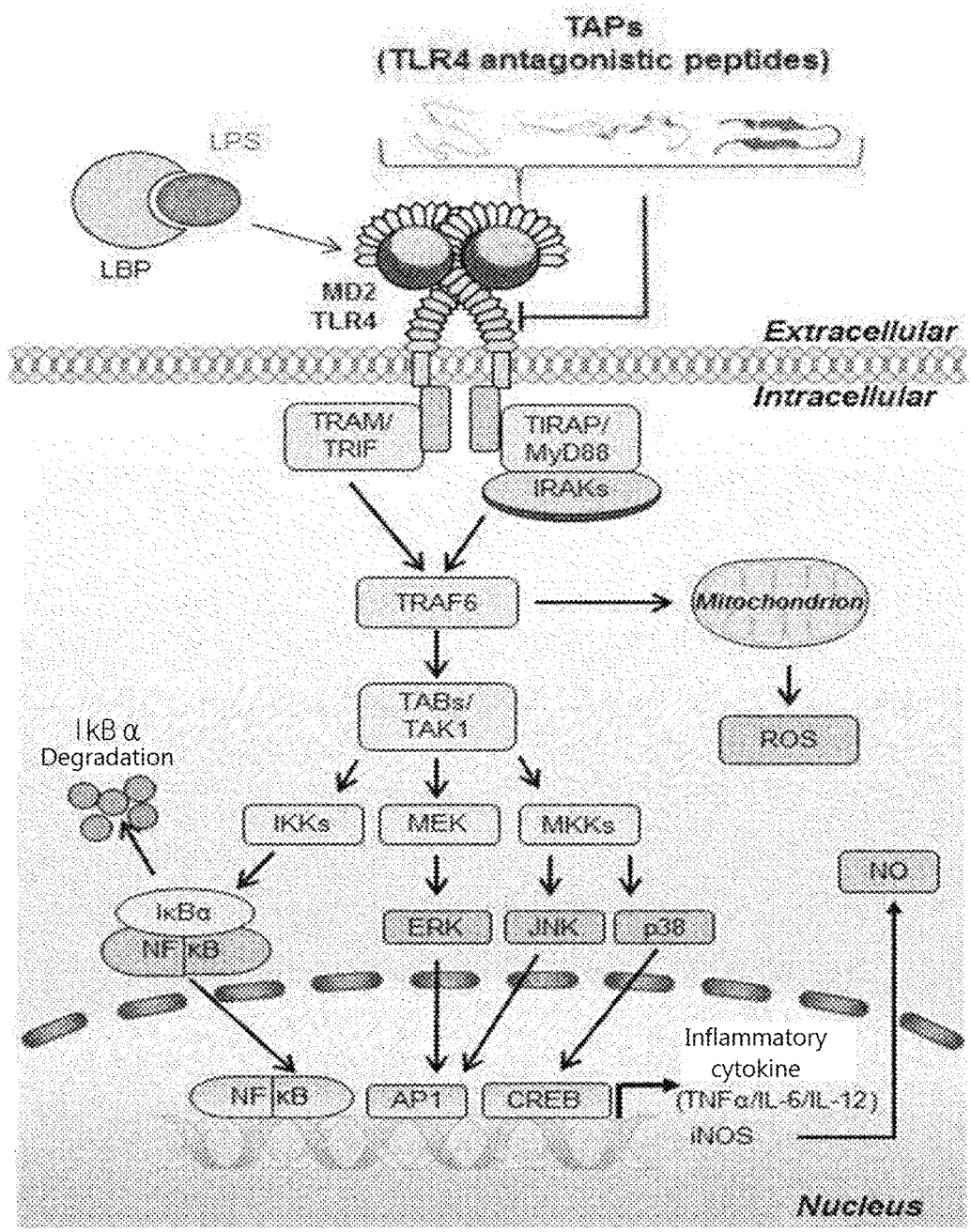
FIG. 12 is a graph schematically illustrating signaling pathways induced by TAPs and TLR4.

As illustrated in FIG. 11, when only LPS was treated, NFκB was uniformly distributed in cytoplasm and nucleus, but when TAPs were treated together, NFκB was present only in cytoplasm. Therefrom, it can be understood that the TAPs according to the present disclosure inhibit the movement of NFκB induced by LPS to the nucleus and inhibit the expression of inflammatory factors expressed by NFκB and the expression of iNOS and ATF3.

INDUSTRIAL APPLICABILITY

The peptide of the present disclosure has an excellent effect of inhibiting the secretion of interleukin-6 (IL-6), NO, and ROS, and the activation of NFκB and MAPKs by inhibiting a TLR4 signaling pathway, and thus can act as TLR4 antagonists, and can be favorably used as a composition for preventing or treating autoimmune diseases and inflammatory diseases associated with TLR4.

The invention claimed is:

1. A peptide represented by the amino acid sequence selected from the group consisting of SEQ ID NOs: 1 to 3.

2. A TLR4 (Toll-like receptor 4) antagonist, comprising a peptide represented by the amino acid sequence selected from the group consisting of SEQ ID NOs: 1 to 3.

3. A method of treating an autoimmune disease by inhibiting a TLR4 signaling pathway, comprising administering a pharmaceutical composition comprising an effective amount of the peptide of claim 1 to a subject in need thereof.

4. The method of claim 3, wherein the TLR4 signaling pathway is induced by lipopolysaccharide (LPS).

5. The method of claim 3, wherein the peptide inhibits interleukin-6 (IL-6), nitrogen oxide (NO), or reactive oxygen species (ROS).

6. The method of claim 3, wherein the peptide inhibits the activity of nuclear factor kappa-light-chain-enhancer of activated B cells (NFκB) or mitogen-activated protein kinases (MAPKs).

7. The method of claim 3, wherein the peptide binds to a toll-like receptor 4 (TLR4)/myeloid differentiation factor 2 (MD2) composite.

8. A method of treating an inflammatory disease by inhibiting a TLR4 signaling pathway, comprising administering a pharmaceutical composition comprising an effective amount of the peptide of claim 1 to a subject in need thereof.

9. The method of claim 8, wherein the TLR4 signaling pathway is induced by lipopolysaccharide (LPS).

10. The method of claim 8, wherein the peptide inhibits interleukin-6 (IL-6), nitrogen oxide (NO), or reactive oxygen species (ROS).

11. The method of claim 8, wherein the peptide inhibits the activity of nuclear factor kappa-light-chain-enhancer of activated B cells (NFκB) or mitogen-activated protein kinases (MAPKs).

12. The method of claim 8, wherein the peptide binds to a toll-like receptor 4 (TLR4)/myeloid differentiation factor 2 (MD2) composite.

* * * * *

SEQUENCE LISTING

```
<160> NUMBER OF SEQ ID NOS: 9

<210> SEQ ID NO 1
<211> LENGTH: 20
<212> TYPE: PRT
<213> ORGANISM: Artificial Sequence
<220> FEATURE:
<223> OTHER INFORMATION: TAP1

<400> SEQUENCE: 1
```

```
Ala Ser Ala Asn Lys Asn Leu Leu Phe Lys Ile Arg Tyr Ser Thr Ala
1               5                   10                  15

Arg Gly Gly Ser
            20

<210> SEQ ID NO 2
<211> LENGTH: 18
<212> TYPE: PRT
<213> ORGANISM: Artificial Sequence
<220> FEATURE:
<223> OTHER INFORMATION: TAP2

<400> SEQUENCE: 2

Ala Met Ala Leu Asp Cys Phe Arg Trp Gly Trp Arg Met Trp Cys Ser
1               5                   10                  15

Ser Gly

<210> SEQ ID NO 3
<211> LENGTH: 18
<212> TYPE: PRT
<213> ORGANISM: Artificial Sequence
<220> FEATURE:
<223> OTHER INFORMATION: TAP3

<400> SEQUENCE: 3

Ala Met Ala Tyr Glu Ile Arg Cys Trp Trp Arg Trp Cys Tyr Thr Ser
1               5                   10                  15

Ser Gly

<210> SEQ ID NO 4
<211> LENGTH: 22
<212> TYPE: DNA
<213> ORGANISM: Artificial Sequence
<220> FEATURE:
<223> OTHER INFORMATION: forward primer for 15-mer peptide

<400> SEQUENCE: 4
ttgatcgcaa ggatcggcta gc                                          22

<210> SEQ ID NO 5
<211> LENGTH: 90
<212> TYPE: DNA
<213> ORGANISM: Artificial Sequence
<220> FEATURE:
<223> OTHER INFORMATION: reverse primer for 15-mer peptide
<220> FEATURE:
<221> NAME/KEY: MISC_FEATURE
<222> LOCATION: (25)..(26)
<223> OTHER INFORMATION: n is a, c, g or t
<220> FEATURE:
<221> NAME/KEY: MISC_FEATURE
<222> LOCATION: (28)..(29)
<223> OTHER INFORMATION: n is a, c, g or t
<220> FEATURE:
<221> NAME/KEY: MISC_FEATURE
<222> LOCATION: (31)..(32)
<223> OTHER INFORMATION: n is a, c, g or t
<220> FEATURE:
<221> NAME/KEY: MISC_FEATURE
<222> LOCATION: (34)..(35)
<223> OTHER INFORMATION: n is a, c, g or t
<220> FEATURE:
<221> NAME/KEY: MISC_FEATURE
<222> LOCATION: (37)..(38)
<223> OTHER INFORMATION: n is a, c, g or t
<220> FEATURE:
<221> NAME/KEY: MISC_FEATURE
<222> LOCATION: (40)..(41)
```

<223> OTHER INFORMATION: n is a, c, g or t
<220> FEATURE:
<221> NAME/KEY: MISC_FEATURE
<222> LOCATION: (43)..(44)
<223> OTHER INFORMATION: n is a, c, g or t
<220> FEATURE:
<221> NAME/KEY: MISC_FEATURE
<222> LOCATION: (46)..(47)
<223> OTHER INFORMATION: n is a, c, g or t
<220> FEATURE:
<221> NAME/KEY: MISC_FEATURE
<222> LOCATION: (49)..(50)
<223> OTHER INFORMATION: n is a, c, g or t
<220> FEATURE:
<221> NAME/KEY: MISC_FEATURE
<222> LOCATION: (52)..(53)
<223> OTHER INFORMATION: n is a, c, g or t
<220> FEATURE:
<221> NAME/KEY: MISC_FEATURE
<222> LOCATION: (55)..(56)
<223> OTHER INFORMATION: n is a, c, g or t
<220> FEATURE:
<221> NAME/KEY: MISC_FEATURE
<222> LOCATION: (58)..(59)
<223> OTHER INFORMATION: n is a, c, g or t
<220> FEATURE:
<221> NAME/KEY: MISC_FEATURE
<222> LOCATION: (61)..(62)
<223> OTHER INFORMATION: n is a, c, g or t
<220> FEATURE:
<221> NAME/KEY: MISC_FEATURE
<222> LOCATION: (64)..(65)
<223> OTHER INFORMATION: n is a, c, g or t
<220> FEATURE:
<221> NAME/KEY: MISC_FEATURE
<222> LOCATION: (67)..(68)
<223> OTHER INFORMATION: n is a, c, g or t

<400> SEQUENCE: 5
aaggccttgg taccgctgcc accmnnmnnm nnmnnmnnmn nmnnmnnmnn mnnmnnmnnm    60
nnmnnmnngc tagccgatcc ttgcgatcaa                                    90

<210> SEQ ID NO 6
<211> LENGTH: 76
<212> TYPE: DNA
<213> ORGANISM: Artificial Sequence
<220> FEATURE:
<223> OTHER INFORMATION: forward primer for 12-mer peptide
<220> FEATURE:
<221> NAME/KEY: MISC_FEATURE
<222> LOCATION: (19)..(20)
<223> OTHER INFORMATION: n is a, c, g or t
<220> FEATURE:
<221> NAME/KEY: MISC_FEATURE
<222> LOCATION: (22)..(23)
<223> OTHER INFORMATION: n is a, c, g or t
<220> FEATURE:
<221> NAME/KEY: MISC_FEATURE
<222> LOCATION: (25)..(26)
<223> OTHER INFORMATION: n is a, c, g or t
<220> FEATURE:
<221> NAME/KEY: MISC_FEATURE
<222> LOCATION: (28)..(29)
<223> OTHER INFORMATION: n is a, c, g or t
<220> FEATURE:
<221> NAME/KEY: MISC_FEATURE
<222> LOCATION: (31)..(32)
<223> OTHER INFORMATION: n is a, c, g or t
<220> FEATURE:
<221> NAME/KEY: MISC_FEATURE
<222> LOCATION: (34)..(35)
<223> OTHER INFORMATION: n is a, c, g or t
<220> FEATURE:
<221> NAME/KEY: MISC_FEATURE
<222> LOCATION: (37)..(38)
<223> OTHER INFORMATION: n is a, c, g or t

```
<220> FEATURE:
<221> NAME/KEY: MISC_FEATURE
<222> LOCATION: (40)..(41)
<223> OTHER INFORMATION: n is a, c, g or t
<220> FEATURE:
<221> NAME/KEY: MISC_FEATURE
<222> LOCATION: (43)..(44)
<223> OTHER INFORMATION: n is a, c, g or t
<220> FEATURE:
<221> NAME/KEY: MISC_FEATURE
<222> LOCATION: (46)..(47)
<223> OTHER INFORMATION: n is a, c, g or t
<220> FEATURE:
<221> NAME/KEY: MISC_FEATURE
<222> LOCATION: (49)..(50)
<223> OTHER INFORMATION: n is a, c, g or t
<220> FEATURE:
<221> NAME/KEY: MISC_FEATURE
<222> LOCATION: (52)..(53)
<223> OTHER INFORMATION: n is a, c, g or t

<400> SEQUENCE: 6
gcccagccgg ccatggccnn knnknnknnk nnknnknnkn nknnknnknn knnktcgagt     60
ggtggaggcg gttcag                                                    76

<210> SEQ ID NO 7
<211> LENGTH: 23
<212> TYPE: DNA
<213> ORGANISM: Artificial Sequence
<220> FEATURE:
<223> OTHER INFORMATION: reverse primer for 12-mer peptide

<400> SEQUENCE: 7
gccagcattg acaggaggtt gag                                            23

<210> SEQ ID NO 8
<211> LENGTH: 18
<212> TYPE: DNA
<213> ORGANISM: Artificial Sequence
<220> FEATURE:
<223> OTHER INFORMATION: primer for 15-mer peptide

<400> SEQUENCE: 8
tgaatttcct gtatgagg                                                  18

<210> SEQ ID NO 9
<211> LENGTH: 21
<212> TYPE: DNA
<213> ORGANISM: Artificial Sequence
<220> FEATURE:
<223> OTHER INFORMATION: primer for 12-mer peptide

<400> SEQUENCE: 9
ttgtgagcgg ataacaattt g                                              21
```